United States Patent [19]

Leoni

[11] Patent Number: 4,867,173
[45] Date of Patent: Sep. 19, 1989

[54] STEERABLE GUIDEWIRE

[75] Inventor: Gianni Leoni, Greve Str., Denmark

[73] Assignee: Meadox Surgimed A/S, Oelstykke, Denmark

[21] Appl. No.: 880,518

[22] Filed: Jun. 30, 1986

[51] Int. Cl.[4] ............................................. A61B 5/00
[52] U.S. Cl. ..................................... 128/772; 604/170
[58] Field of Search .............................. 128/656-658, 128/772; 604/95, 164, 170

[56] References Cited

U.S. PATENT DOCUMENTS

| | | | |
|---|---|---|---|
| 2,118,631 | 5/1938 | Wappler | 604/170 |
| 3,547,103 | 12/1970 | Cook | 604/95 |
| 3,789,841 | 2/1974 | Antoshkiw | 128/772 |
| 4,020,829 | 5/1977 | Willson et al. | 128/657 |
| 4,538,622 | 9/1985 | Samson et al. | 128/772 |
| 4,545,390 | 10/1985 | Leary | 128/772 |
| 4,548,206 | 10/1985 | Osborne | 128/772 |

FOREIGN PATENT DOCUMENTS 2505191 11/1982 France ............................... 128/772

Primary Examiner—Max Hindenburg
Attorney, Agent, or Firm—Blum Kaplan

[57] ABSTRACT

A small diameter steerable guidewire with uniform flexibility in its distal region particularly well suited for PTCA use is provided. The guidewire has a diameter of less than 0.50 mm and is formed from an elongated substantially cylindrical main core wire with a distal cylindrical region of reduced diameter at the distal end of the core wire. A safety wire is attached to the distal end of the region of reduced diameter and a safety tip attached to the distal end of the safety wire and coil. The safety wire and coil may be formed of a radio opaque material so the position of the wire can be accurately determined when in use.

16 Claims, 2 Drawing Sheets

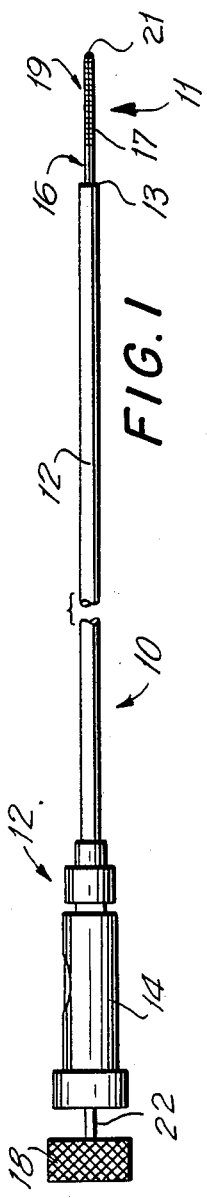
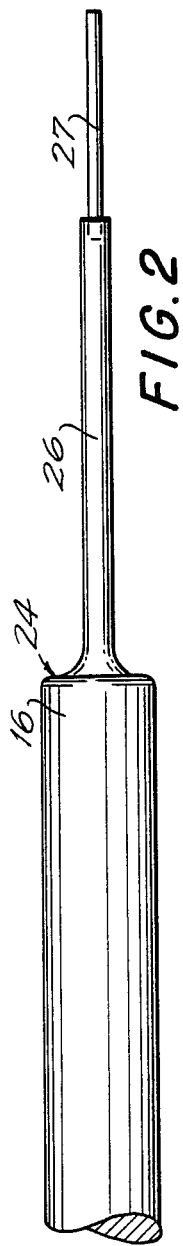
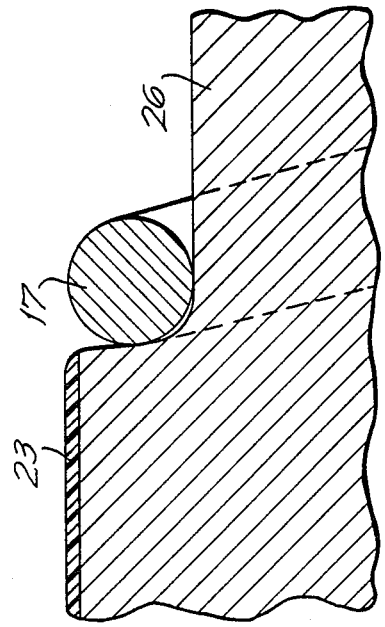

STEERABLE GUIDEWIRE

BACKGROUND OF THE INVENTION

This invention relates in general to guidewires, and in particular to a small diameter steerable guidewire for use in procedures in narrow vascular lumens, such as percutaneous transluminal coronary angioplasty (PTCA).

The use of small dimension guidewires in cardiovascular systems has become an absolute necessity. It is difficult to penetrate the stenotic areas within regions of narrow lumens by the use of conventional guidewires, therefore, the traumatic risk to the patient increases with the decrease of available lumen area. Narrower guidewires lessen this risk. Additionally, a very low thrombogenicity, traumatic sensitive torque control, equal unidirectional flexibility, radiopacity, low friction, constant diameter, smooth transition among its segmented parts, being shapeable to a desired configuration and having an equal bending sensitivity in all directions along the length of its distal end are highly desirable features in a small diameter guidewire.

Small diameter guidewires having diameters less than 0.02 inch are known in the art as disclosed in U.S. Pat. No. 4,545,390. In the steerable guidewire disclosed in this patent, the main wire has a Teflon coated core wire, formed with a tapered region at its distal region. A helically wound spring is attached to the tapered region and is shown extending beyond the tapered distal region to a rounded tip. The diameter of the core wire and helically wound spring at its distal region does not exceed 0.02 inch.

A similar guidewire is shown in U.S. Pat. No. 4,538,622. This guidewire is again formed with a main core wire having a tapered distal region. The main wire is wrapped at its tapered distal end by two coils, at least one coil being of a radio opaque material. The coils extend beyond the distal end of the tapered wire, and the diameter of the distal end wire with coils is less than 0.02 inch. In U.S. Pat. No. 4,554,929 a similar Teflon coated core wire having a tapered distal region includes a spring on the tapered region which extends beyond the distal end thereof. A rounded tip 21 is secured to the distal end of the spring and is coupled to the tapered region by a safety wire.

These prior art guidewires have been satisfactory; however, they suffer from the disadvantage that they have limited flexibility in regions of the distal end and do not have uniform directional flexibility along the length of the spring coil.

Accordingly, it is desirable to provide a small diameter guidewire for use in cardiovascular vessels having improved flexibility and increased uniform directional bendability along the length of the coil spring region of increased flexibility.

SUMMARY OF THE INVENTION

Generally speaking, in accordance with the invention, a steerable guidewire of reduced diameter having improved flexibility and bendability at its distal region is provided. The guidewire includes an elongated main core wire having a cylindrical configuration with a proximal end and a distal end. The main core wire is coated with a frictionless material and is formed with a shoulder at the distal end of the main core where the diameter is reduced to receive a coil spring to provide a smooth transition between the main core wire and the coil. The coil is helically wound about the distal cylindrical region and abuts the shoulder and extends to a rounded tip at the distal end of the guidewire. The diameter of the guidewire is generally between about 0.25 to 0.50 mm, or 0.01 to 0.02 inch.

It is an object of this invention to provide an improved steerable guidewire of reduced diameter.

Another object of this invention is to provide a guidewire having uniform directional flexibility along the length of the distal region.

A further object of this invention is to provide a small guidewire with equal bending sensitivity at its distal end in all directions.

Still another object of the invention is to provide a small guidewire having improved torque transmission.

Still a further object of this invention is to provide a guidewire of small dimensions which is less traumatic to the vascular system.

Yet a further object of the invention is to provide a small dimension guidewire having varying degrees of flexibility at its distal region.

Yet another object of the invention is to provide an improved steerable guidewire having a diameter 0.25 and 0.50 mm which is suitable for PTCA.

Still other objects and advantages of the invention will in part be obvious and will in part be apparent from the specification and drawings.

The invention accordingly comprises features of construction, combination of elements, and arrangement of parts which will be exemplified in the construction hereinafter set forth and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 illustrates a guidewire in accordance with the invention and guide catheter assembly suitable for use with a PTCA balloon catheter;

FIG. 2 is a partial elevational view of the distal end of the guidewire in accordance with the invention guidewire with the coil removed;

FIG. 3 is an enlarged sectional view of the shoulder formed at the distal end of the main core wire section of the guidewire of FIG. 1;

DETAILED DESCRIPTION OF THE PREFERRED EMBODIMENTS

Figure 4:
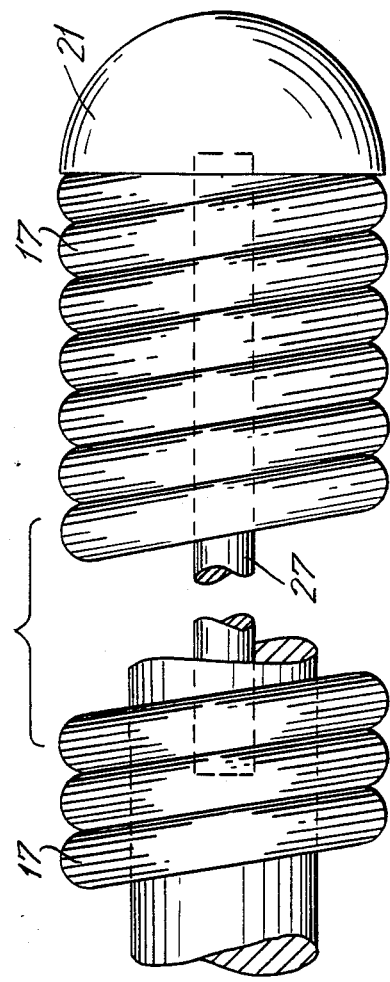
FIG. 4 is a partial elevational view of the distal end of the guidewire showing the coil and tip.

In FIG. 1, a guidewire and guide catheter assembly 10 including a guidewire 11 and a guide catheter 12 constructed and arranged in accordance with the invention, is shown. Guide catheter 12 includes an elongated tubular body of relatively flexible material having an axial extending opening 13 and a connector fitting 14 formed at its proximal end. Guide catheter 12 is dimensioned so that guidewire 11 may be selectively manipulated in the manner to be described in more detail below. The exterior dimension of guide catheter 12 is selected so that a working catheter of a desired type may be inserted thereover into the cardiovascular system of a patient. Typically, in the small dimension guidewire and guide catheter assemblies discussed herein, the working catheter will be a balloon-type dilatation catheter suitable for percutaneous transluminal coronary angioplasty (PTCA).

Guidewire 11 is an elongated, relatively rigid, cylindrical member, including a main core wire 16 with a proximal region 22 terminating in a control knob 18 and a distal region 19 terminating in a rounded tip 21. A helical coil 17 is wound about the distal region 19 of main core wire 16. In the illustration of FIG. 1, distal region 19 is shown extending through opening 13 at the distal end of guide catheter 12.

In order to be suitable for PTCA use, guidewire 11 must be provided having a diameter which may range from 0.25 to 0.60 mm. A Teflon ® DuPont trademark for PTFE (polytetrafluoroethylene) coating 23, as shown in FIG. 33, is provided on main core wire 16 in order to increase lubricity.

Referring now to FIG. 2, a partial elevational view of distal region 19 of main core wire 16 with coil 17 and tip 21 removed is shown in detail. The outer dimension of main core wire 16 is uniform over its entire length, and terminates at its distal end in a shoulder 24 extending into a distal cylindrical region 26 of reduced diameter. Distal cylindrical region 26 is substantially uniformly bendable and is formed by grinding the distal end of main wire 16. A mini-cylindrical safety wire 27 is joined at its proximal end to the distal end of distal cylindrical region 26. Tip 21 is mounted to the distal end of safety wire 27 as shown in FIG. 4. As will be described in more detail below, safety wire 27 may be formed of a highly radio opaque material for assisting in locating tip 21 of guidewire 11 when inserted in the cardiovascular system.

The length of coil 17 is relatively short compared to the overall length of guidewire 11. Generally, the length of uniform diameter of main core wire 16 is between about 50 and 200 centimeters. The diameter along this length is generally uniform and about 0.25 to 0.50 mm, or between about 0.01 to 0.02 inch. Coil 17 may be between about 20 to 40 cm in length and is fixed to main core wire 16 at shoulder region 24. The outside diameter of coil 17 is substantially the same as the outside diameter of main core wire 16 which is generally coated with a frictionless material, such as Teflon. This coating along its entire length facilitates movement of guidewire 11 within guide catheter 12, the balloon catheter and the coronary vessels. The diameter of uniformly bendable distal cylindrical region 26 is less than that of main core wire 16. Generally, it is greater than about ½ of that of main core wire 16 and provides for the thickness of coil 17 to provide a substantially uniform outer diameter along the entire length of guidewire 11. In the preferred embodiments in accordance with the invention, distal cylindrical region 26 has a diameter of about 0.35 mm or about 0.14 inch.

Main core wire 16 is formed from a suitable flexible metallic material, such as stainless steel wire. In the preferred embodiments in accordance with the invention, main core wire 16 is formed of stainless steel No. 302 or No. 304. Any such steel having such physical properties according to AISI/AMS is suitable.

Uniformly bendable distal cylindrical region 26 is aligned along the principal longitudinal axis of main core wire 16. Region 26 is utilized to impart increased flexibility at the distal end of guidewire 11 and maintain the torsional torque thereof. Distal cylindrical region 26 is also formed of a flexible metallic material, preferably stainless steel as described above.

In the illustrated embodiments, a cylindrical safety ribbon 27 is joined by welding to the distal region of distal cylindrical section 26. Safety ribbon 27 is preferably formed of a radio opaque material, such as iridium, platinum, gold or the like. Use of such radio opaque materials makes the tip of guidewire 11 visible to a fluoroscope, or similar radiographic instrument. Safety wire 27 is generally provided, having a length of about 10 to 50 mm and is formed with a diameter less than 0.1 mm. Preferably the diameter of safety wire 27 is about 0.076 mm.

In addition to providing safety ribbon 27 of a highly radio opaque material, coil 17 may also be formed of a radio opaque material of the type described above. In the preferred embodiments in accordance with the invention, it has been found that platinum/wolfram combinations including between about 6–8 weight percent platinum are suitable for producing long lengths of wire for producing coil 17. Generally, about 180 to 200 cm length of wire is required to produce coil 17 having a length of between about 20 to 40 cm in length. Various other alloys have different weight ratios from 10–30% iridium or platinum in platinum-rhodium zirconium stabilized may also be utilized.

Figure 5:
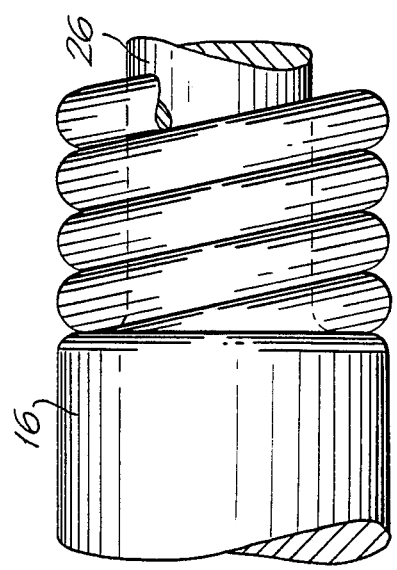
FIG. 5 is a partial elevational view of the shoulder region of the guidewire.

Coil 17 is placed about distal cylindrical region 26 and extends to shoulder 24 at the distal end of main core wire 16 and is point welded thereat. This is shown in FIG. 5. As noted above, a smooth transition between main core wire 16 and coil 17 is provided to insure smooth movement of guidewire 11 and prevent the possibility of damage to the vessels. Safety wire 27 is also welded to the distal end of distal cylindrical region 26 and tip 21 is welded to safety wire 27 and coil 17. Safety wire 27 is generally more flexible than uniformly bendable distal cylindrical region 26 and is provided in a length of from 10 to 50 mm with a diameter of less than 0.1 mm. Tip 21 may also be formed of the radio opaque materials disclosed above.

Different degrees of flexibility may be obtained by varying the various dimensions of guidewire 11. For example, since safety wire 27 is substantially more flexible than distal cylindrical region 26, the relative lengths of the two regions will impart different flexibility to guide wire 11. Additionally, by increasing the diameter of distal cylindrical region 26, the flexibility of that region will be correspondingly decreased. Safety wire 27 may be formed with a desired bend so that guide catheter 12 may be steered into a side branch of the cardiovascular system. The angle and particular shape of the bend can be chosen in accordance with the known procedures for PTCA. By manipulation of control knob 18 the distal end of guidewire 11 may be extended through the distal end of guide catheter 12 so that guidewire 11 will bend in accordance with the preset bend to safety wire 27. Upon rotation of knob 18, guidewire 11 may be steered to the desired position within the cardiovascular system. Similarly, guidewire 11 will assume the straightened configuration when distal region 19 is retracted into guide catheter 12.

Figure 6:
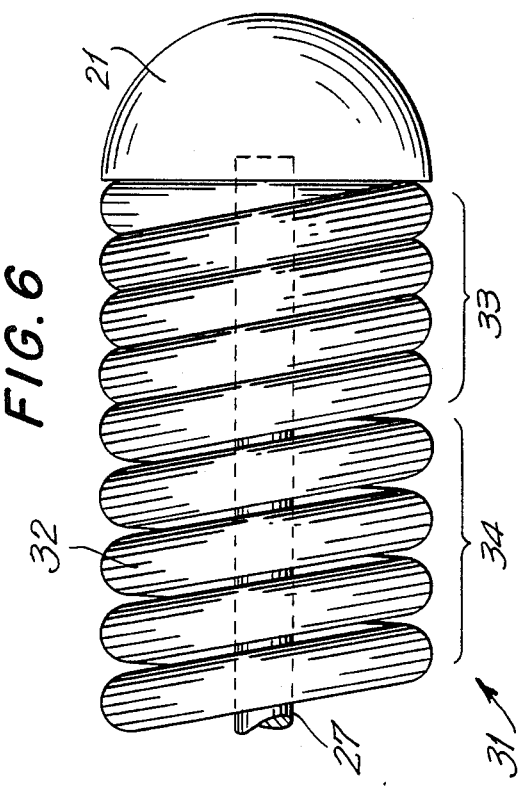
FIG. 6 is an elevational view of the distal end and coil section of a guidewire constructed in accordance with an embodiment of the invention.

In FIG. 6 a guidewire 31 constructed in accordance with another embodiment of the invention is shown. Guidewire 31 is formed in the same manner as guidewire 11, with the exception of a coil 32 which is formed with regions of different pitch to provide regions of differing flexibility. Specifically, coil 32 includes a distal region 33 wherein the turns of the helix are tightened, which imparts added directional stability. Distal region 33 may be provided in a length of about 5 mm. Coil 32 also includes a mid-region 34 having an open pitch to provide a region of more flexibility than distal tip 33. Accordingly, by varying the pitch of coil 32 along its length, regions of different flexibility may be readily provided.

Accordingly, by providing a small diameter steerable guidewire having a distal cylindrical region of reduced diameter with a coil over the region of reduced diameter, a steerable guidewire having a distal region of uniform bendability is provided. Additionally, by providing a more distal region of reduced diameter of a highly radiopague material with a rounded tip fixed thereon, a small diameter steerable guidewire suitable for PTCA use is also provided. The highly radio opaque material facilitates location of the distal end of the guidewire by fluoroscopic and radiographic devices. Additionally, the entire coil may be formed of a radio opaque material to enhance the marking of the position of the guidewire.

It will thus be seen that the objects set forth above, among those made apparent from the preceding description, are efficiently attained and, since certain changes may be made in the above article without departing from the spirit and scope of the invention, it is intended that all matter contained in the above description and shown in the accompanying drawings shall be interpreted as illustrative and not in a limiting sense.

It is also to be understood that the following claims are intended to cover all the generic and specific features of the invention herein described and all statements of the scope of the invention which, as a matter of language, might be said to fall therebetween.

What is claimed is:

1. A small diameter steerable guidewire comprising:
an elongated core wire having a main wire portion with a substantially cylindrical configuration of uniform diameter with a proximal end and a distal end and having a distal cylindrical region of reduced diameter at the distal end;
the distal cylindrical region being of uniform diameter which is smaller than the main wire portion;
the distal end of the main wire portion formed with a shoulder region with the distal cylindrical region extending from the main wire portion at the shoulder region, the shoulder region providing a sharp transition between the main wire portion and the distal cylindrical region for providing a guidewire having improved uniform bendability;
a substantially cylindrical safety wire having a diameter less than the distal cylindrical region secured to the distal end of the distal cylindrical region and extending therefrom;
a coil attached to the distal end of the main wire portion surrounding the distal cylindrical region;
the coil having a diameter substantially equal to the diameter of the main wire portion for providing a smooth transition between the outer surface of the main wire portion and coil;
a safety tip secured to the coil at its distal end, with the safety wire extending from the distal end of the distal cylindrical region to the tip;
the coil having a distal region located towards the safety tip and a proximal region located towards the main wire portion, and wherein the turns of the coil are more tightly packed, considered in the axial direction, in the distal region of the coil than in the proximal region of the coil to provide increased bendability to the coil at the proximal region of the coil; and
the length of the coil being small relative to the length of the main wire portion.

2. The guidewire of claim 1, wherein the main wire portion is coated with a friction less material.

3. The guidewire of claim 2, wherein the frictionless material is polytetrafluoroethylene.

4. The guidewire of claim 1, wherein the diameters of the main wire portion and the coil are substantially equal and less than 0.50 mm.

5. The guidewire of claim 1, wherein the coil is formed from a radio opaque material.

6. The guidewire of claim 5, wherein the radio opaque material is an alloy of wolfram and platinum.

7. The guidewire of claim 1, wherein the wires are formed of stainless steel.

8. The guidewire of claim 1, wherein the coil attachment to the distal end of the main wire portion is a point welding attachment to the shoulder region of the main wire portion.

9. A small diameter steerable guidewire, comprising:
an elongated core wire having a main wire portion with a substantially cylindrical configuration of uniform diameter with a proximal end and a distal end and having a distal cylindrical region of reduced diameter at the distal end;
the distal cylindrical region being of uniform diameter which is smaller than the main wire portion;
the distal end of the main wire portion formed with a shoulder region with the distal cylindrical region being coaxial with the main wire portion, extending from the main wire portion at the shoulder region, the shoulder region providing a sharp transition between the main wire portion and the distal cylindrical region for providing a guidewire having improved uniform bendability;
a substantially cylindrical safety wire which is coaxial with the main wire, the safety wire having a diameter less than the distal cylindrical region and being secured to the distal end of the distal cylindrical region and extending therefrom;
the substantially cylindrical safety wire secured to the distal end of the distal cylindrical region coaxial with the main wire;
a coil attached to the distal end of the main wire portion surrounding the distal cylindrical region;
the coil having a diameter substantially equal to the diameter of the main wire portion for providing a smooth transition between the outer surface of the main wire portion and coil;
a safety tip secured to the coil at its distal end, with the safety wire extending from the distal end of the distal cylindrical region to the tip;
the coil having a distal region located towards the safety tip and a proximal region located towards the main wire portion, and wherein the turns of the coil are more tightly packed, considered in the axial direction, in the distal region of the coil than in the proximal region of the coil to provide increased bendability to the coil at the proximal region of the coil; and
the length of the coil being small relative to the length of the main wire portion.

10. The guidewire of claim 9, wherein the safety wire is formed of a radio opaque material.

11. The guidewire of claim 10, wherein the radio opaque material is an alloy of wolfram and platinum.

12. The guidewire of claim 9, wherein the coil attachment to the distal end of the main wire portion is a point welding attachment to the shoulder region of the main wire portion.

13. A small diameter steerable guidewire, comprising:
- an elongated cylindrical wire having a main wire portion with a diameter less than 0.50 mm with a proximal end and a distal end and the main wire portion coated with a frictionless material, the distal end being formed with a shoulder region;
- a cylindrical distal region of a smaller diameter than the main wire portion formed at the distal end of the main wire portion with the shoulder region constituting a sharp transition between the greater diameter of the main wire portion and the smaller diameter of the distal cylindrical region for providing a guidewire having improved uniform bendability;
- a cylindrical safety wire secured to the distal end of the distal cylindrical region;
- a coil having a distal end and a proximal end attached to the distal end of the main wire portion and arranged in turns which surround the distal cylindrical region and the safety wire, the coil having a uniform diameter equal to the diameter of the main core wire portion for forming a smooth transition along the outer surface of the main wire portion and the coil;
- a safety tip secured to the distal end of the coil and safety wire;
- the coil having a distal region located towards the safety tip and a proximal region located towards the main wire portion, and wherein the turns of the coil are more tightly packed, considered in the axial direction, in the distal region of the coil than in the proximal region of the coil to provide increased bendability to the coil at the proximal region of the coil; and
- the length of the coil being small relative to the length of the main wire portion.

14. The guidewire of claim 13, wherein the coil is formed of a radio opaque material.

15. The guidewire of claim 13, wherein the safety wire is made of a radio opaque material.

16. The guidewire of claim 13, wherein the coil attachment to the distal end of the main wire portion is a point welding attachment to the shoulder region of the main wire portion.

* * * * *